(12) United States Patent
Kelleher et al.

(10) Patent No.: US 8,030,005 B2
(45) Date of Patent: Oct. 4, 2011

(54) METHOD FOR DETECTING ANTIGEN SPECIFIC OR MITOGEN-ACTIVATED T CELLS

(75) Inventors: Anthony Dominic Kelleher, Bangor (AU); John James Zaunders, Kingsford (AU)

(73) Assignee: St. Vincent's Hospital Sydney Limited (AU)

( * ) Notice: Subject to any disclaimer, the term of this patent is extended or adjusted under 35 U.S.C. 154(b) by 334 days.

(21) Appl. No.: 12/293,222

(22) PCT Filed: Mar. 20, 2007

(86) PCT No.: PCT/AU2007/000342
§ 371 (c)(1),
(2), (4) Date: Feb. 2, 2009

(87) PCT Pub. No.: WO2007/106939
PCT Pub. Date: Sep. 27, 2007

(65) Prior Publication Data
US 2009/0221005 A1     Sep. 3, 2009

(30) Foreign Application Priority Data
Mar. 20, 2006 (AU) ............................... 2006901400

(51) Int. Cl.
*G01N 33/53* (2006.01)
(52) U.S. Cl. ........................................ 435/7.1; 435/7.24
(58) Field of Classification Search .................. None
See application file for complete search history.

(56) References Cited

U.S. PATENT DOCUMENTS
2005/0196386 A1    9/2005  Blazar et al.

FOREIGN PATENT DOCUMENTS
WO    WO00 11476 A    3/2000

OTHER PUBLICATIONS

Kotani et al. Blood. Nov. 15, 2001;98(10):3162-4.*
Wang et al. The Journal of Immunology, 2002, 169: 4717-4722.*
Supplementary European Search Report dated Mar. 4, 2009, for European Patent Application No. 07718589.0; Applicant, St. Vincent's Hospital Sydney Limited.
Sanchez, Joaquin et al., Kinetic of Regulatory $CD25^{high}$ and Activated $CD134^+(OX40)$ Tlymphocytes During Acute and Chronic Graft-*Versus*-Host Disease After Allogeneic Bone Marrow Transplantation. British Journal of Haematology, 126, 697-703.
Miura, Y. et al. Regulation of OX40 Gene Expression in Graft-Versus-Host Disease. Transplantation Proceedings, 37, 57-61 (2005).
van Amelsfort, J. M. R. et al. "CD4 + CD25 Regulatory T Cells in Rheumatoid Arthritis." Arthritis & Rheumatism, vol. 50, No. 9, Sep. 2004, pp. 2775-2785.
Gummert, J. F. et al. "Pharmacodynamics of Mycophenolic Acid in Heart Allograft Recipients: Correlation of Lymphocyte Proliferation and Activation With Pharmacokinetics and Graft Histology." Transplantation, vol. 70, 1038-1049, No. 7, Oct. 15, 2000.
Barten, M. J. et al. "Flow Cytometric Quantitation of Calcium-Dependent and -Independent Mitogen-Stimulation of T cell Functions in Whole Blood: Inhibition by Immunosuppressive Drugs in vitro." Journal of Immunological Methods 253 (2001) 95-112.
Barten, M. J. et al. "Novel Assays of Multiple Lymphocyte Functions in Whole Blood Measure New Mechanisms of Action of Mycophenolate Mofetil in vivo." Transplant Immunology 10 (2002) 1-14.
International Search Report prepared by the Australian Patent Office on May 21, 2007, for International Application No. PCT/AU2007/000342; Applicant, St. Vincent's Hospital Sydney Limited.
Endl. et al., "Coexpression of CD25 and OX40 (CD134) receptors delineates autoreactive T-cells in type 1 diabetes"; Diabetes, vol. 55 (Jan. 2006) pp. 50-60.
Streeter et al., "CD25 expression distinguishes functionally different distinct alloreactive $CD4^+CD134^+(OX40^+)$ T-cell subsets in acute graft-versus-host disease"; Biol. Blood Marrow Transplant (May 2004) vol. 10, No. 5, pp. 298-309.
Nolte-'t et al., "Identification of a $CD4^+CD25^+$T cell subset committed in vivo to suppress antigen-specific T cell responses without additional stimulation"; Eur. J Immunol. (2004) vol. 34, pp. 3016-3027.
Zauders et al., "Early proliferation of $CCR5^+CD38^{+++}$antigen-specific $CD4^+$Th1 effector cells during primary HIV-1 infection"; Blood (Sep. 1, 2005) vol. 106, No. 5, pp. 1660-1667.
Giacomelli et al., "T lymphocytes in the synovial fluid of patients with active rheumatoid arthritis display CD134-OX40 surface antigent"; Clinical and Experimental Rheumatology (2001) vol. 19, pp. 317-320.
Seddiki et al., "Expression of interleukin (IL)-2 and IL-7 receptors discriminates between human regulatory and activated T cells"; JEM (Jul. 2006) vol. 203, No. 7, pp. 1693-1700.
Markert et al., "Choriocarcinoma-induced suppression of lymphocyte activity"; Invest. Allergol. Clin. Immunol. (2000) vol. 10, No. 6, pp. 323-326.

* cited by examiner

*Primary Examiner* — Zachary Skelding
(74) *Attorney, Agent, or Firm* — Sheridan Ross P.C.

(57) ABSTRACT

The present invention comprises a method for the quantitative or qualitative detection of antigen-specific CD4+ T cells and/or CD8+ T cells in a subject, said method comprising quantitatively or qualitatively detecting the expression of cell surface marker CD25 and one or more of cell surface markers CD134 and CD137 in a suitable lymphocyte-containing sample from said subject in response to exposure to an antigen. A method for determining the immunocompetence of a subject and a method for isolating antigen-specific CD4+ and/or CD8+ T cells is also disclosed.

16 Claims, 7 Drawing Sheets

US 8,030,005 B2

METHOD FOR DETECTING ANTIGEN SPECIFIC OR MITOGEN-ACTIVATED T CELLS

CROSS REFERENCE TO RELATED APPLICATIONS

This application is a national stage application under 35 U.S.C. 371 of PCT Application No. PCT/AU2007/000342 having an international filing date of 20 Mar. 2007, which designated the United States, which PCT application claimed the benefit of Australian Patent Application No. 2006901400 filed 20 Mar. 2006, the entire disclosure of each of which are hereby incorporated herein by reference.

FIELD OF THE INVENTION

The present invention relates to methods for the detection of antigen-specific CD4+ or CD8+ T cells or the measurement of the general immunocompetence of a subject.

BACKGROUND OF THE INVENTION

The CD4+ subpopulation of T lymphocytes (CD4+ T cells) play a major role in the body's defense against intracellular pathogens such as pathogenic intracellular bacteria (e.g. *Mycobacteria*) and fungus (e.g. *Candida*), viruses and protozoa. In particular, the CD4+ T cells help to regulate the cell-mediated immune response to infection by such intracellular pathogens, and indeed are often referred to as "helper" T cells, by promoting a variety of immune responses from other cells (e.g. promotion and maturation of B lymphocytes and antibody responses, activation of macrophages, and enhancement of natural killer (NK) cell and CD8+ cytotoxic T cell (CTL) activity) through the release of cytokines in response to antigenic stimulation. Such antigenic stimulation is achieved by the recognition by "primed" CD4+ T cells (i.e. CD4+ T cells which have been previously exposed to an antigen to become "antigen-specific CD4+ T cells") of an antigen presented by any antigen presenting cell expressing an appropriate class II major histocompatibility complex (MHC) protein. As mentioned above, one of the immune responses, or "effector functions", brought about by stimulated CD4+ T cells is the activation of macrophages. Activated macrophages play a vital role in killing pathogens at sites of infection through increased phagocytic activity (i.e. activated macrophages show an increased ability to phagocytose pathogens) and other activities. The interaction between antigen-specific CD4+ T cells and macrophages forms the basis of the so-called delayed type hypersensitivity response (DTH) which has been exploited in various skin tests to determine whether a subject has been previously exposed or "sensitised" to a particular antigen (e.g. an antigen from a pathogen or an allergen). One well known type of DTH skin test is the Mantoux test which employs tuberculin as an antigen in the testing for latent tuberculosis (caused by *Mycobacterium tuberculosis*) in a subject or for determining whether a subject has been previously vaccinated with bacille Calmette-Guerin (BCG) tuberculosis vaccine.

The Mantoux test, and other similar delayed-type hypersensitivity skin tests such as the BioMerieux Multitest, have been widely used in the clinic and diagnostic and research laboratories for detecting antigen-specific responses, presumptively mediated by CD4+ T cells. They do, however, require a considerable amount of time to perform (i.e. in order to achieve a readable result), require the patient to return for the reading of the result, and there is considerable intra-operator variability in the application and reading of these tests. These problems combine to limit their effective use. For example, for the Mantoux test, any DTH response must be observed some 2-3 days after administration of the tuberculin antigen, which may not be feasible or desirable for the effective testing of persons living in remote locations. Moreover, assessment of skin test results are relatively subjective, leading to qualitative, rather than quantitative results.

Apart from DTH skin tests, antigen-specific CD4+ T cells can be detected, and indeed measured, by other methods. For example, using peripheral blood mononuclear cells (PBMC), antigen-specific CD4+ T cells can be measured by the method known as the lymphoproliferation assay (LPA). However, this method, which utilises the ability of CD4+ T cells to proliferate in vitro and involves detecting the incorporation of $^3$H-thymidine into newly synthesised DNA after 6-7 days in culture, has several limitations making it unattractive for diagnostic laboratories, namely: (i) the use of high levels of radionucleotides; (ii) a long "turnaround" time; (iii) the requirement for lengthy processing of blood samples to prepare PBMC; (iv) the dependence on carefully screened human serum, with variability from batch to batch; (v) the need for culture techniques which require a high level of training; (vi) the fact that the response can only be attributed to CD4+ T cells if CD4+ T cells are first purified; and vii) substantial inter- and intra-assay variability making standardisation between laboratories problematical. Presently, LPAs are seldom performed except in research laboratories.

Another example is a flow cytometric version of the LPA, using carboxy-fluorescein diacetate, succinimidyl ester (CFSE)-labelled PBMC (1). This assay has been widely used in research laboratories, and although it has the distinct advantages that it does not use radioactivity and also allows for the direct identification of responding CD4+ T cells, it still suffers from the other disadvantages of the LPA. In addition, this assay has the disadvantage that the flow cytometric analysis must be very carefully performed since the number of relevant cells can be very low, often amidst substantial background staining.

A further example is the so-called intracellular cytokine (ICC) assay. This has become a relatively widely used assay in research laboratories, and it allows for the direct detection of antigen-specific CD4+ T cells in whole blood cultures (2). This assay is, however, quite labour-intensive; requiring either a 6 hour culture with whole protein antigens (2 hours for antigen processing and presentation, plus 4 hours with brefeldin A) or 6 hour culture with peptides and brefeldin A. Further, when samples are obtained late in the day, they require a processing step late at night, or are otherwise left until the next day, which is not optimal. Moreover, a 2 hour intracellular staining step is then required after the culture, followed by flow cytometric analysis. Automation of the ICC assay is possible (3), but not generally available. Also, standardisation between laboratories is problematical.

Accordingly, there is no method for detecting antigen-specific CD4+ T cells amongst those that are presently available that are readily applicable to the clinic and diagnostic and research laboratories. Further, of those that are suitable for use in diagnostic laboratories, various problems and difficulties with them have made them unpopular. However, assays for detecting antigen-specific CD4+ T cells are not the only kind of immune response assay that have fallen from favour in diagnostic laboratories. That is, the response of lymphocytes of the immune system to the polyclonal mitogen, phytohaemagglutinin (PHA), has been previously widely used as a measure of general T cell immunocompetence (e.g. for cases of suspected primary immunodeficiency (4)); however, since this assay is based on the $^3$H-thymidine LPA, with the exception that the cells are harvested at day 3, it is subject to essentially the same disadvantages as the LPA.

A simpler whole blood method has been proposed in which small aliquots of anti-coagulated samples of whole blood are incubated with an antigen or PHA for 4 hours (up to 24 hours), and activation measured by up-regulation of the early T-cell activation marker antigen, CD69, on CD4+ T cells, by flow cytometry (5). This whole blood assay, with a short turn-around time and very simple cell surface readout, was an attractive approach. However, in the hands of the present applicant, it has been found that while the assay is useful for measuring polyclonal PHA responses, it is not sufficiently specific for detecting antigen-specific CD4+ T cells since an unfeasibly large number of CD4+ T cells up-regulate CD69 in response to antigen indicating a lack of specificity with this readout. Further, it was found that the analysis of results was complicated by the presence of CD69 on a small but significant subset of CD4+ T cells ex vivo.

Another example of a whole blood assay for antigen-specific CD4+ T cells that is in use is the Quantiferon® whole blood stimulation assay (CSL Limited, Melbourne, VIC, Australia). In this assay, following antigenic stimulation, the plasma is collected and assayed for IFN-γ by ELISA. However, as with the standard LPA, the response is not confirmed as being due to CD4+ T cells, since much IFN-γ is produced by CD8+ T cells, particularly in response to viral antigens, as well as by NK cells present in the cultures. At present, this assay is only licensed for detection of responses to *M. tuberculosis*. However, the assay has been observed to give high numbers of indeterminate results in young paediatric populations. There is a second assay for the detection of IFN-γ responses stimulated by *M. tuberculosis* known as the T spot TB assay approved for use in the Europe. This assay is an ELIspot based method, requiring separation of PBMC before plating out in an ELIspot plate. The assay appears to have similar specificity and sensitivity, but a lower rate of indeterminate results in paediatric and immuno-suppressed patients.

Accordingly, there remains a need for an alternative and relatively simple and cost effective method for detecting, particularly, antigen-specific CD4+ T cells, but also antigen-specific CD8+ T cells.

While investigating the kinetics of the up-regulation of the cell surface marker antigen CD25 (a transmembrane protein that is the α-chain of the interleukin-2 (IL-2) receptor) and cell division using CFSE-labelled PBMC, the present applicant found that CD25 was highly up-regulated on CD4+ T cells in response to antigen or mitogen from 24 hours onwards, preceding cell division which begins at about 48 hours onwards. At the same time, the kinetics of expression of certain co-stimulation cell surface proteins such as CD134 (OX40) and CD137 (4-1BB) was being investigated, and it was found that up-regulation of these proteins also occurred from 24 hours onwards. Genetic studies in mouse models have shown that the interaction between OX40 on CD4+ T cells and OX40 ligand (OX40L) on antigen-presenting cells is crucial for the generation of "memory" CD4+ T cells (i.e. primed CD4+ T cells that have developed into so-called memory cells able to confer immediate protection as well as the capacity to mount a more rapid and effective immune response to antigenic stimulation), and the promotion of effector CD4+ T cells survival after antigen priming. Since it had been previously reported that CD134 expression on CD4+ T cells peaks at 24-48 hours after stimulation of the T cell receptor by antigen or mitogen, and returns to baseline about 120 hours later (6), the present applicant therefore investigated whether CD25 and CD134 were co-expressed just prior to 48 hour (i.e. a timepoint that corresponded with maximal CD134 expression, but prior to the commencement of cell division), using whole blood cultures stimulated with antigens or mitogens, and might therefore be used as the basis of a relatively simple and cost effective method for the detection and/or measurement of antigen-specific CD4+ T cells. It was found that these cell surface markers for antigen-specific CD4+ T cells can be readily measured by flow cytometry after 40-44 hours incubation with antigen using sodium heparin anti-coagulated whole blood samples. Therefore, the method combines simplicity of set up (i.e. without the need for preparation of PBMC) with a simple flow cytometry read-out (i.e. without the need to permeabilise cells and detect cytokines). Further, it was found that the method has a surprisingly low background (<0.03% of CD4+ T cells), and by using the method, it has to-date been possible to readily detect specific CD4+ T cells responses to antigens contained in preparations of mycobacterial antigens, tetanus toxoid, Cytomegalovirus (CMV) lysate, vaccinia lysate and peptides of Human Immunodeficiency Virus (HIV-1). Moreover, it has been found that the method can also be used in assessing the broader responses to mitogens such as PHA and Staphylococcal enteroantigen B (SEB), as a measure of general immunocompetence. Still further, the method has application in cell sorting of antigen-specific or mitogen-activated CD4+ T cells, whereby fixation and permeabilisation steps may be avoided.

SUMMARY OF THE INVENTION

In a first aspect, the present invention provides a method for the quantitative or qualitative detection of antigen-specific CD4+ T cells and/or CD8+ T cells in a subject, said method comprising quantitatively or qualitatively detecting the expression of cell surface marker CD25 and one or more of cell surface markers CD134 and CD137 in a suitable lymphocyte-containing sample from said subject in response to exposure to an antigen.

Preferably, the method of the first aspect comprises the following steps:
(i) culturing a suitable lymphocyte-containing sample from the subject in the presence of an antigen; and
(ii) quantitatively or qualitatively detecting co-expression of CD25 and one or more of CD134 and CD137 in the cultured sample.

Preferably, the lymphocyte-containing sample is a whole blood sample.

Preferably, the step of detecting expression of CD25 and one or more of CD134 and CD137 is performed within about 48 hours of commencement of the culturing of the lymphocyte-containing sample in the presence of the antigen.

Preferably, the step of detecting expression of CD25 and one or more of CD134 and CD137 consists of quantitatively or qualitatively detecting CD25 and CD134 on CD4+ T cells or quantitatively or qualitatively detecting CD25 and CD137 on CD8+ T cells.

Preferably, the method is used for the quantitative or qualitative detection of antigen-specific CD4+ T cells.

In a second aspect, the present invention provides a method for measuring the immunocompetence of a subject, said method comprising quantitatively or qualitatively detecting the expression of cell surface marker CD25 and one or more of cell surface markers CD134 and CD137 in a suitable lymphocyte-containing sample from said subject in response to exposure to an antigen and/or mitogen.

Preferably, the method of the second aspect comprises the following steps:
(i) culturing a suitable lymphocyte-containing sample from the subject in the presence of an antigen and/or mitogen; and
(ii) quantitatively or qualitatively detecting co-expression of CD25 and one or more of CD134 and CD137 in the cultured sample.

Preferably, the lymphocyte-containing sample is a whole blood sample.

Preferably, the step of detecting expression of CD25 and one or more of CD134 and CD137 is performed within about 48 hours of commencement of the culturing of the lymphocyte-containing sample in the presence of the antigen and/or mitogen.

Preferably, the step of detecting expression of CD25 and one or more of CD134 and CD137 consists of quantitatively or qualitatively detecting CD25 and CD134 on CD4+ T cells or quantitatively or qualitatively detecting CD25 and CD137 on CD8+ T cells.

Preferably, the method is used for the quantitative or qualitative detection of antigen-specific or mitogen-activated CD4+ T cells.

DETAILED DESCRIPTION OF THE INVENTION

Figure 1:
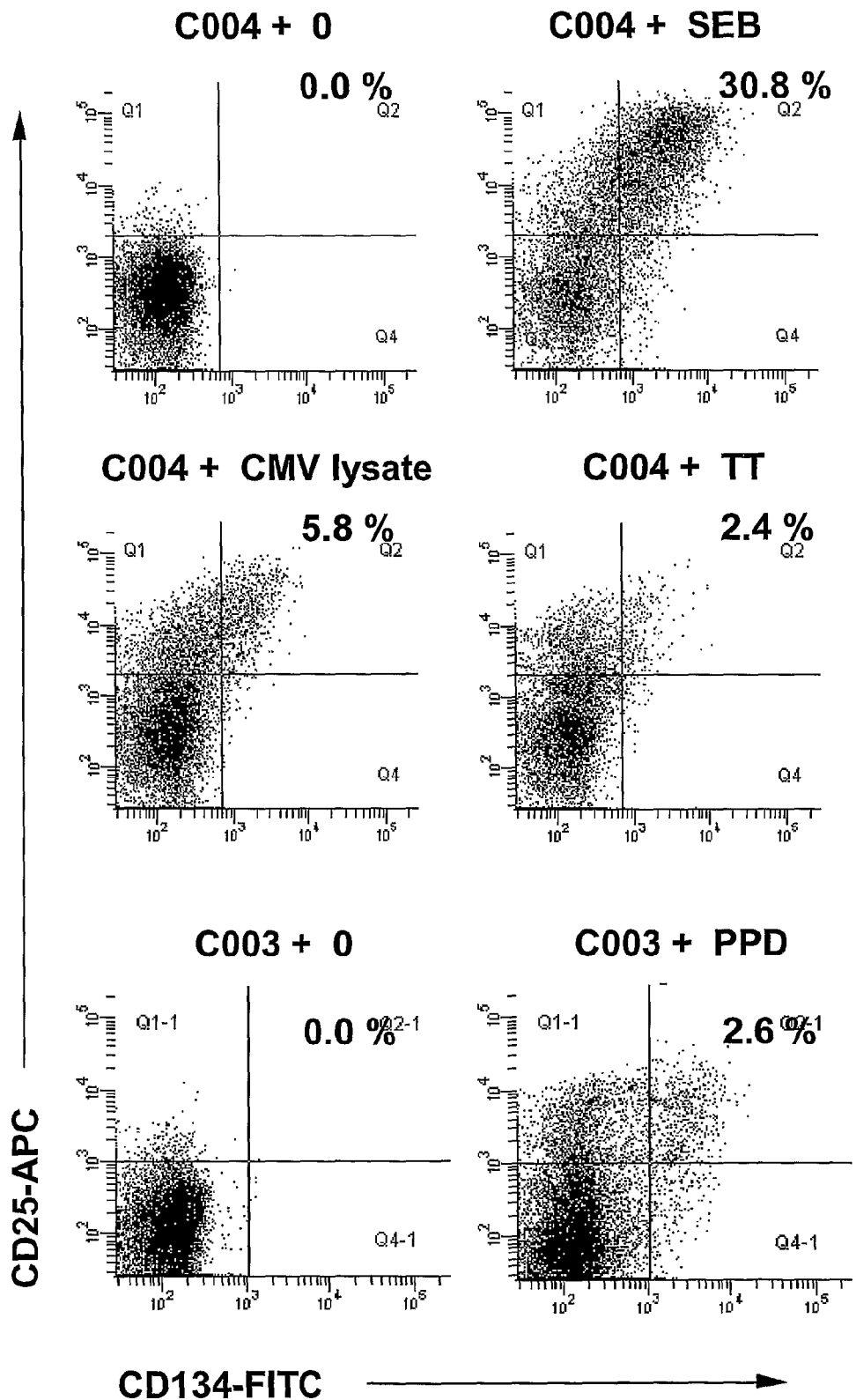
FIG. 1 provides histograms from a representative healthy adult control subject showing staining for CD25+CD134+ CD4+ T cells in the control culture (+0) compared with staining for CD25+CD134+ CD4+ T cells in response to SEB, CMV, tetanus toxoid (TT), and purified protein derivative (PPD) from *M. tuberculosis*, respectively. The percentage of CD25+CD134+ CD4+ T cells is shown for each histogram.

The present applicant has found that the detection of expression of cell surface markers, CD25 and CD134 and/or CD137, provides a useful means for detecting and/or measuring antigen-specific CD4+ T cells and/or CD8+ T cells in cultured lymphocyte-containing samples, particularly whole blood samples, from a subject.

The term "antigen-specific", used in relation to CD4+ T cells or CD8+ T cells, is to be understood as meaning that the T cells are able to specifically bind and respond to the particular antigen of interest. Additionally, it is to be understood that the CD4+ T cells or CD8+ T cells described as "antigen specific" are not T regulatory cells ($T_{REG}$ cells).

In a first aspect, the present invention provides a method for the quantitative or qualitative detection of antigen-specific CD4+ T cells and/or CD8+ T cells in a subject, said method comprising quantitatively or qualitatively detecting expression of cell surface marker CD25 and one or more of cell surface markers CD134 and CD137 in a suitable lymphocyte-containing sample from said subject in response to exposure to an antigen.

Preferably, the method of the first aspect comprises the following steps:
(i) culturing a suitable lymphocyte-containing sample from the subject in the presence of an antigen; and
(ii) quantitatively or qualitatively detecting co-expression of CD25 and one or more of CD134 and CD137 in the cultured sample.

Preferably, the lymphocyte-containing sample is a whole blood sample. Such a whole blood sample can be obtained from the subject by any method well known to persons skilled in the art (e.g. by cannula and the use of blood sample vials). A suitable anticoagulant agent may be added to the whole blood sample to prevent clotting. A particularly suitable anticoagulant agent is sodium heparin which can be conveniently used by employing any commercially available heparinised blood sample vials. Preferably, anticoagulant agents which chelate calcium ions ($Ca^{2+}$), such as acid-citrate dextrose (ACD) or ethylene diaminetetraacetic acid (EDTA), are avoided as these may interfere with lymphocyte function by preventing calcium influx (9). Accordingly, it is preferable that whole blood samples, for use in the method of the first aspect, are collected in heparinised blood sample vials.

The step of culturing the lymphocyte-containing sample (e.g. whole blood sample) may be in accordance with any method well known to persons skilled in the art. For a whole blood sample, the sample may be, for example, mixed with a suitable culture medium (e.g. Iscove's modified Dulbecco's medium) and antigen, and incubated at 37° C. The antigen will be selected in accordance with the intended antigen-specific CD4+ T cells and/or CD8+ T cells to be detected. Thus, for example, for testing for latent tuberculosis or prior vaccination with BCG, the selected antigen may be tuberculin or tuberculosis specific antigens such as early secretory antigenic target (ESAT-6) and culture filtrate protein-10 (CFP-10). Similarly, for testing for Hepatitis C, the selected antigen may be Hepatitis C virus (HCV) core antigen or nonstructural protein 3 (NS3), while testing for CMV may utilise phosphoprotein 65 (pp65) or a CMV lysate. For HIV-1, the selected antigen may be recombinant p24 or pools of overlapping peptides from Gag, Env, Pol, or other HIV-1 accessory genes.

Apart from purified proteins (native or recombinant) such as tuberculin and HIV-1 p24, the antigen may be, for example, a bacterial or viral lysate, killed whole virus, antigenic protein fragment (including synthetic antigenic peptides), an overlapping peptide pool (7, 8) or optimised antigenic peptides, whole killed or fixed bacterial, fungal or yeast antigenic preparations or virally infected cells or antigen-pulsed antigen presenting cells. The antigen may be bound to a suitable carrier molecule or used in combination with an adjuvant.

Preferably, the step of detecting expression of CD25 and one or more of CD134 and CD137 is performed before a substantial number of the cells present in the culture have divided. Accordingly, under standard culturing conditions (e.g. 37° C. in a humidified atmosphere of 5% $CO_2$ in air, and using a standard culture medium suitable for the culture of lymphocytes), the detecting step is preferably performed within 60 hours and, more preferably, within 48 hours of commencement of the culturing of the lymphocyte-containing sample in the presence of an antigen. Moreover, it is preferable that the detecting step is performed after the elapse of a sufficient period for co-expression of the cell surface markers (i.e. CD25, CD134 and/or CD137) to be substantially up-regulated. Accordingly, under standard culturing conditions, it is more preferable that the detecting step is performed within about 24 to 48 hours of commencement of the culturing of the lymphocyte-containing sample in the presence of an antigen, and most preferably, within about 40 to 44 hours of commencement of the culturing of the lymphocyte-containing sample in the presence of an antigen.

While the method may involve detecting expression of CD25 and one or more of CD134 and CD137, it is preferable that the method consists of quantitatively or qualitatively detecting CD25 and CD134 on CD4+ T cells or quantitatively or qualitatively detecting CD25 and CD137 on CD8+ T cells.

In this regard, it has been found that few, if any, CD4+ or CD8+ T cells other than antigen-specific CD4+ or CD8+ T cells express these combinations of cell surface markers ex vivo, and this thereby enables the detecting step to be performed against a very low "background" of CD25 and CD134 co-expression or CD25 and CD137 co-expression. As a consequence, the method of the first aspect of the present invention may be used, in particular, to detect rare antigen-specific CD4+ T cells (e.g. present in the culture at frequencies of less than 0.1% of the total CD4+ T cells).

The step of detecting the cell surface markers may be performed in accordance with any method well known to persons skilled in the art. Such a method may involve the use of labelled monoclonal antibodies that specifically bind to one of the cell surface markers, CD25, CD134 and CD137, and, preferably, the use of flow cytometry. In this regard, persons skilled in the art will understand that following binding with suitable, labelled monoclonal antibodies (e.g. anti-CD25 and anti-CD134 antibodies), samples may be fixed with a suitable fixing agent (e.g. paraformaldehyde, which may be used at 1% in phosphate-buffered saline (PBS)) to permit the subsequent quantification or qualitative determination of the cell surface markers (e.g. by the use of flow cytometry) as convenient (e.g. following transport from the site of collection and culture of the lymphocyte-containing sample, to a flow cytometry laboratory). Accordingly, in the context of the preferred times, given above, for performing the detecting step, it is to be understood that the "staining" (i.e. with suitable monoclonal antibodies labelled with a fluorescent dye(s)) and "fixing" of the cultured samples need only be performed within the given preferred time period. That is, it is to be understood that where the staining and fixing is initiated 44 hours after commencement of the culturing of the lymphocyte-containing sample in the presence of an antigen, but the actual quantification or qualitative determination of the cell surface markers is not done until later (e.g. 12 to 24 hours later), that nevertheless amounts to performing the detecting step within the most preferred time period of about 40 to 44 hours of commencement of the culturing of the lymphocyte-containing sample in the presence of antigen.

The method of the first aspect may further comprise isolating cells expressing CD25 and one or more of CD134 and CD137. The isolating step may be performed in accordance with any method well known to persons skilled in the art, for example, by utilising the cell sorting function available on many flow cytometers.

The method of the first aspect of the present invention particularly allows for the quantitative or qualitative detection of antigen-specific CD4+ T cells (i.e. the method allows for monitoring of CD4+ T cell recall responses). The method may therefore be useful for detection of antigen-specific CD4+ T cells against pathogenic intracellular bacteria (e.g. *Mycobacteria, Clostridium* and *Helicobacter*), fungus (e.g. *Candida, Aspergillus* and *Cryptococcus*), viruses (e.g. Cytomegalovirus (CMV), Human Immunodeficiency Virus (HIV)-1, Epstein-Barr virus (EBV), Influenza Virus, Measles Virus, Mumps Virus, Rubella Virus, Hepatitis B Virus (HBV), Hepatitis C Virus (HCV), Herpes Simplex Virus (HSV)-1, HSV-2, JC Virus and Kaposi's Sarcoma Herpesvirus), and protozoa (e.g. *Toxoplasma, Pneumocystis, Cryptosporidium* and *Plasmodium*) extracellular bacteria (e.g. *Escherichia coli, Streptococcus* spp., *Neisseria* spp., *Haemophilus* spp., *Pseudomonas* spp.) and toxoids (tetanus toxoid, Diptheria toxoid). The method may also be useful for detection of antigen-specific CD4+ T cells against autoantigens (e.g. insulin, gliadin, acetyl choline receptor, myelin basic protein, DNA and chromatin) and allergens (e.g. house dust mite proteins or grass pollen proteins).

Preferably, the antigen is selected from the group consisting of tuberculin, HCV core antigen, HCV NS3, CMV pp65, CMV lysate, HSV-1 lysate, HSV-2 lysate, JC Virus lysate, vaccinia lysate, tetanus toxoid (TT), purified protein derivative (PPD) from *Mycobacterium tuberculosis, Streptococcus* antigen streptokinase (SK), HIV-1 p24 and pools of overlapping peptides from Gag, Env, Pol or other HIV-1 accessory genes.

The subject may be human or another animal of veterinary significance (e.g. livestock animals, race horses, and companion animals). The subject can also be a laboratory animal such as a mouse or monkey for use as, for example, a model of human disease or in the development of vaccines, wherein it is of particular interest to analyse various aspects of the immune response.

In a second aspect, the present invention provides a method for measuring the immunocompetence of a subject, said method comprising quantitatively or qualitatively detecting the expression of cell surface marker CD25 and one or more of cell surface markers CD134 and CD137 in a suitable lymphocyte-containing sample from said subject in response to exposure to an antigen and/or mitogen.

Preferably, the method of the second aspect comprises the following steps:
(i) culturing a suitable lymphocyte-containing sample from the subject in the presence of an antigen and/or mitogen; and
(ii) quantitatively or qualitatively detecting co-expression of CD25 and one or more of CD134 and CD137 in the cultured sample.

Preferably, the lymphocyte-containing sample is a whole blood sample. As with the method of the first aspect, the whole blood sample can be obtained from the subject by any method well known to persons skilled in the art, but may be conveniently obtained through the use of a cannula and a heparinised blood sample vial. Again, anticoagulant agents which chelate calcium ions ($Ca^{2+}$) are preferably to be avoided as these may interfere with lymphocyte function.

The step of culturing the lymphocyte-containing sample (e.g. whole blood sample) may be in accordance with any method well known to persons skilled in the art. Thus, for a whole blood sample, the sample may be mixed with a suitable culture medium and antigen and/or mitogen, and incubated at 37° C.

Preferably, in the method of the second aspect of the present invention, the step of culturing the lymphocyte-containing sample involves culturing in the presence of a mitogen. The mitogen may be selected from those mitogens well known to persons skilled in the art, for example, the mitogen may be selected from the group consisting of PHA, phorbol myristyl acetate (PMA), ionomycin, SEB, toxic shock syndrome toxin (TSST), Staphylococcal enterotoxin A (SEA), concanavalin A (Con A), pokeweed mitogen, and anti-CD3 monoclonal antibody optionally in combination with CD28 co-stimulation and/or anti-CD2 monoclonal antibody.

Alternatively, in the method of the second aspect of the present invention, the step of culturing the lymphocyte-containing sample involves culturing in the presence of an antigen. Apart from purified proteins (native or recombinant) such as tuberculin, the antigen may again be, for example, a bacterial or viral lysate, an antigenic protein fragment (including synthetic antigenic peptides), or an overlapping peptide pool (7, 8). The antigen may be bound to a suitable carrier molecule or used in combination with an adjuvant.

Preferably, the antigen is selected from the group consisting of tuberculin, HCV core antigen, HCV NS3, CMV pp65, CMV lysate, HSV-1 lysate, HSV-2 lysate, vaccinia lysate, tetanus toxoid (TT), purified protein derivative (PPD) from *Mycobacterium tuberculosis, Streptococcus* antigen streptokinase, HIV-1 p24, and pools of overlapping peptides from Gag, Pol, Env or other HIV-1 accessory genes.

Preferably, the step of detecting expression of CD25 and one or more of CD134 and CD137 is performed before a substantial number of the cells present in the culture have divided. Accordingly, the detecting step is preferably performed within 60 hours and, more preferably, within 48 hours of commencement of the culturing of the lymphocyte-containing sample in the presence of an antigen and/or mitogen. Moreover, it is preferable that the detecting step is performed after the elapse of a sufficient period for expression of the cell surface markers (i.e. CD25, CD134 and/or CD137) to be substantially up-regulated. Accordingly, it is more preferable that the detecting step is performed within about 24 to 48 hours of commencement of the culturing of the lymphocyte-containing sample in the presence of an antigen and/or mitogen, and most preferably, within about 40 to 44 hours of commencement of the culturing of the lymphocyte-containing sample in the presence of an antigen and/or mitogen.

While the method may involve detecting co-expression of CD25 and one or more of CD134 and CD137, it is preferable that the method consists of quantitatively or qualitatively detecting CD25 and CD134 on CD4+ T cells or quantitatively or qualitatively detecting CD25 and CD137 on CD8+ T cells.

The step of detecting the cell surface markers may be performed in accordance with any method well known to persons skilled in the art. Preferably, the detecting step comprises the use of flow cytometry. As with the method of the first aspect, flow cytometry may be delayed (e.g. for 12 to 24 hours), if the cultured lymphocyte-containing sample is suitably fixed. Thus, where the detecting step comprises the use of suitable, monoclonal antibodies (e.g. anti-CD25 and anti-CD134 antibodies) labelled with, for example, fluorescent dye(s) and the use of flow cytometry, the cultured lymphocyte-containing sample may be stained and fixed 44 hours after commencement of the culturing of the sample with an antigen and/or mitogen but with the quantification or qualitative determination of the cell surface markers (e.g. by flow cytometry) performed later. As such, it will be understood that the detecting step has nevertheless been performed within the most preferred time period of about 40 to 44 hours of commencement of the culturing of the lymphocyte-containing sample in the presence of antigen and/or mitogen.

The method of the second aspect may further comprise isolating cells expressing CD25 and one or more of CD134 and CD137. The isolating step may be performed in accordance with any method well known to persons skilled in the art, for example, by utilising the cell sorting function available on many flow cytometers.

Again, the subject may be human or another animal of veterinary or laboratory significance.

In order that the nature of the present invention may be more clearly understood, preferred forms thereof will now be described with reference to the following non-limiting examples.

EXAMPLES

Example 1

Human Whole Blood CD25/CD134 Assay

Materials and Methods

Subjects

Healthy adult volunteers were recruited from university and hospital staff. Three subjects were inoculated with vaccinia, for occupational reasons, in accordance with local occupational health and safety guidelines, and provided longitudinal samples, as described elsewhere (10). An HIV-positive long-term non-progressor, LTNP-001, who has a readily detectable CD4+ T cell response to HIV-1 p24 (7) was also examined.

Reagents

The mitogen, phytohaemagglutinin (PHA; Sigma, St Louis, Mo., United States of America), was used in whole blood cultures at a final concentration of 5 μg/ml. Staphylococcal enterotoxin B (SEB; Sigma) was used at a final concentration of 1 μg/ml.

CMV lysate was prepared as previously described (7) and used at a final concentration of 1/250.

Vaccinia antigen for in vitro assays was prepared as described elsewhere (10), following propagation of the NYCBH strain in HeLa cells. Whole viral lysate of infectious intracellular mature virus was prepared by multiple freeze-thawing of infected cells, followed by removal of cell debris by centrifugation at 700 g for 10 min. Viral antigen was further treated by heat inactivation at 56° C. for 30 min, which reduced the infectious titre by a factor of $10^6$ (data not shown). Vaccinia lysate was used at a final concentration of 1/250. A control lysate of uninfected HeLa cells was also prepared in parallel, and used at the same final concentration.

Mycobacterial antigen prepared as PPD from *M. tuberculosis* (MTB) was obtained from Staten Serum Institute (Denmark). PPD was used at a final concentration of 5 μg/ml.

Tetanus toxoid (TT) was obtained from Commonwealth Serum Laboratories (CSL Limited, Melbourne, VIC, Australia). TT was used according to the manufacturer's directions at a final concentration of 2 Lf U/ml.

HIV-1 p24 (Protein Sciences, Meriden, Conn., United States of America) was used at a concentration of 5 μg/ml as previously described (7). CD3-PerCP-Cy5.5, CD4-PE-Cy7, CD8-APC-Cy7, CD25-APC, CD134-PE, and CD134-FITC conjugated monoclonal antibodies were obtained from Becton-Dickinson (San Jose, Calif., United States of America).

Lymphoproliferation Assays (LPA)

Peripheral blood mononuclear cells (PBMC) were isolated by Ficoll-Hypaque density gradient centrifugation as previously described (7). $1 \times 10^5$ PBMC were incubated per well in 96-well round-bottom plate for 6 days in RPMI 1640 (JRH, Melbourne, VIC, Australia) containing 10% human serum (Cambrex, East Rutherford, N.J., United States of America). Quadruplicate cultures were set up containing no additive (control), or different antigens or mitogens. 0.5 μCi of $^3$H-thymidine (Amersham, Buckinghamshire, United Kingdom) was added per well and incubated for a further 18 hr, followed by cell harvesting (Canberra Packard) and counting on a TopCount scintillation counter (Packard Instrument Co. Meriden, Conn., United States of America). The mean of the replicate counts for each antigen or mitogen was divided by the mean for the control cultures, giving a stimulation index (SI). Cpm in control wells were in the range of 124-428 cpm.

The CFSE assay of proliferation of CD4+ T cells was performed as previously described (7).

Intracellular Cytokine (ICC) Assay

A whole blood intracellular cytokine (ICC) assay, based on a previously published method (2), using 6-colour flow cytometry, was used to measure vaccinia-specific CD4+ T cells, as described elsewhere (7, 10). Briefly, 0.5 ml of Na Heparin-anticoagulated whole blood was incubated with costimulatory antibodies CD28 and CD49d in the presence of no additive (control), SEB, or vaccinia or control lysates for 2 hr at 37° C., followed by a further 4 hr incubation with 10 μg/ml Brefeldin A (Sigma-Aldrich). At the end of this incubation, EDTA (Sigma) was added to the cultures at a final concentration of 2 μM, for 15 min at room temperature (RT). Intracellular staining for cytokines was performed as previously described (7). Briefly, 100 μl from these cultures was then incubated with 1 ml of FACSLysing Solution for 10 min at RT, washed once with 2 ml PBA. Pellets were then incubated with 0.5 ml FACS Permeabilising Solution for 10 min at RT, and washed once with 2 ml PBA. Cells were then incubated with mAb for 30 min at RT in the dark, then washed once with 2 ml phosphate-buffered saline (PBS) containing 0.5% bovine serum albumin and 0.1% sodium azide (PBA), and resuspended in 0.5% paraformaldehyde/phosphate buffered saline (PF/PBS).

For analysis, 300,000 events were collected, as previously described (8). T lymphocytes were first gated on CD3-PerCP-Cy5.5 versus side scatter, then on CD4-PE-Cy7-positive/CD8-APC-Cy7-negative cells, and CD69-APC+ IFN-γ-FITC+ cells were analysed. This method has a validated cut-off for positive results of 0.08% of CD4+ T cells, based on background results plus 3 times the standard deviation, from analysis of sixteen HIV-negative controls (Munier et al, unpublished results)

Whole Blood CD25/CD134 Assay 0.25 ml of Na Heparin-anticoagulated whole blood was mixed with 0.25 ml Iscove's Modified Dulbecco's Medium (IMDM; JRH) in 5 ml sterile polystyrene screw cap jars (Biolabs, Melbourne, VIC, Australia). Antigens and mitogens were added at the specified concentrations, and cultures were incubated, with the cap loosely attached, at 37° C. for 40 hr in a humidified atmosphere of 5% $CO_2$ in air. Negative control cultures comprised mixed whole blood and IMDM only, in the absence of any antigens. Positive control cultures contained either PHA or SEB. These positive and negative culture controls were included in every experiment.

Flow Cytometry

Flow cytometry of whole blood cultures was performed after fixation on a dual-laser LSR II flow cytometer (Becton-Dickinson) using FACSDiva v4.1 software. T lymphocytes were first identified using a CD3-PerCP-Cy5.5 vs side scatter gate, followed by gating on CD3+ CD4-PE-Cy7+ T cells. Also, CD8-APC-Cy7 staining was used to exclude CD8+ T cells from the CD4+ gate. CD3+CD4+CD8− cells were then analysed for staining with CD25-APC and CD134-PE. In some experiments, CD25-APC and CD134-FITC were used, as indicated. All monoclonal antibodies were obtained from Becton-Dickinson. A minimum of 50,000 events were analysed. Compensation was checked using lymphocytes stained with individual fluorochromes, and then confirmed with cells stained simultaneously for CD3-PerCP-Cy5.5, CD4-PE-Cy7, CD8-APC-Cy7, CD56-APC, CD19-PE, and CD14-FITC (Becton-Dickinson). Further controls included individual tubes in which APC, PE or FITC antibodies were not included (data not shown).

Results

Negative Controls and Responses to Mitogens and Antigens

Background co-expression of CD25 and CD134 (OX40) on CD4+ T cells in a control culture (+0) is shown in FIG. 1. From results obtained in 31 separate experiments, the background mean was 0.0062% and the standard deviation was 0.0082%. Therefore, the cut-off for a positive result was calculated as the mean+3× standard deviation: 0.0062%+3× 0.0082%=0.03%.

Representative histograms showing responses to the polyclonal mitogen SEB are also shown in FIG. 1, demonstrating the very high proportions of CD4+ T cells which respond to this mitogen.

Representative histograms showing responses, in healthy adult controls, to recall antigens: CMV lysate, TT, and PPD, are also shown in FIG. 1.

Kinetics of Co-Expression of CD25 and CD134

Figure 2:
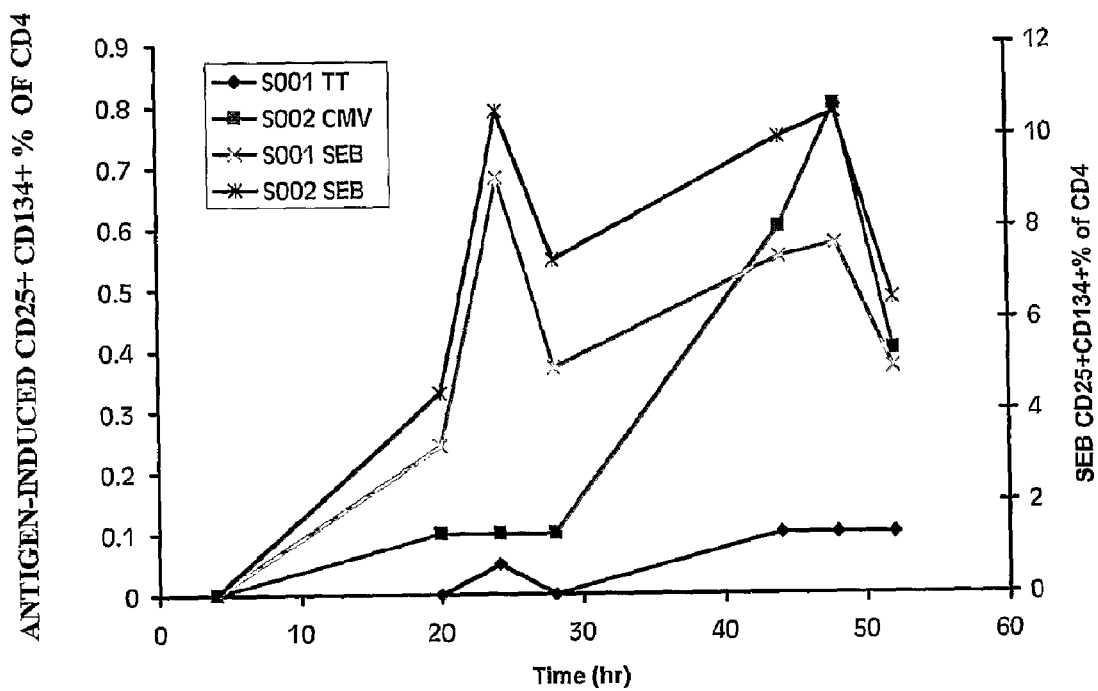
FIG. 2 provides the results of staining for CD25+CD134+ CD4+ T cells at different incubation times from 4 to 52 hours, for two different healthy adult control subjects (S001 and S002), in response to TT (S001; left axis), CMV (S002; left axis) and SEB (S001 and S002; right axis), respectively.

The kinetics of the development of CD25+CD134+ CD4+ T cells in whole blood cultures are shown for two subjects in FIG. 2. The results show that antigen-specific CD4+ T cell responses are optimally detected at 44 hr. This time point precedes the time at which CD4+ T cells may begin to proliferate in vitro, as detected by the CFSE LPA (data not shown). Therefore, the CD4+ T cells measured as CD25+CD134+ at 44 hr appear to reflect the number present in the original whole blood sample.

The responses to SEB in these experiments peaked briefly at 24 hr, but a second peak of similar magnitude was observed by 44 hr (FIG. 2). Therefore, both antigen-specific and polyclonal responses to mitogens can be measured at the same time point, 44 hr.

Figure 3:
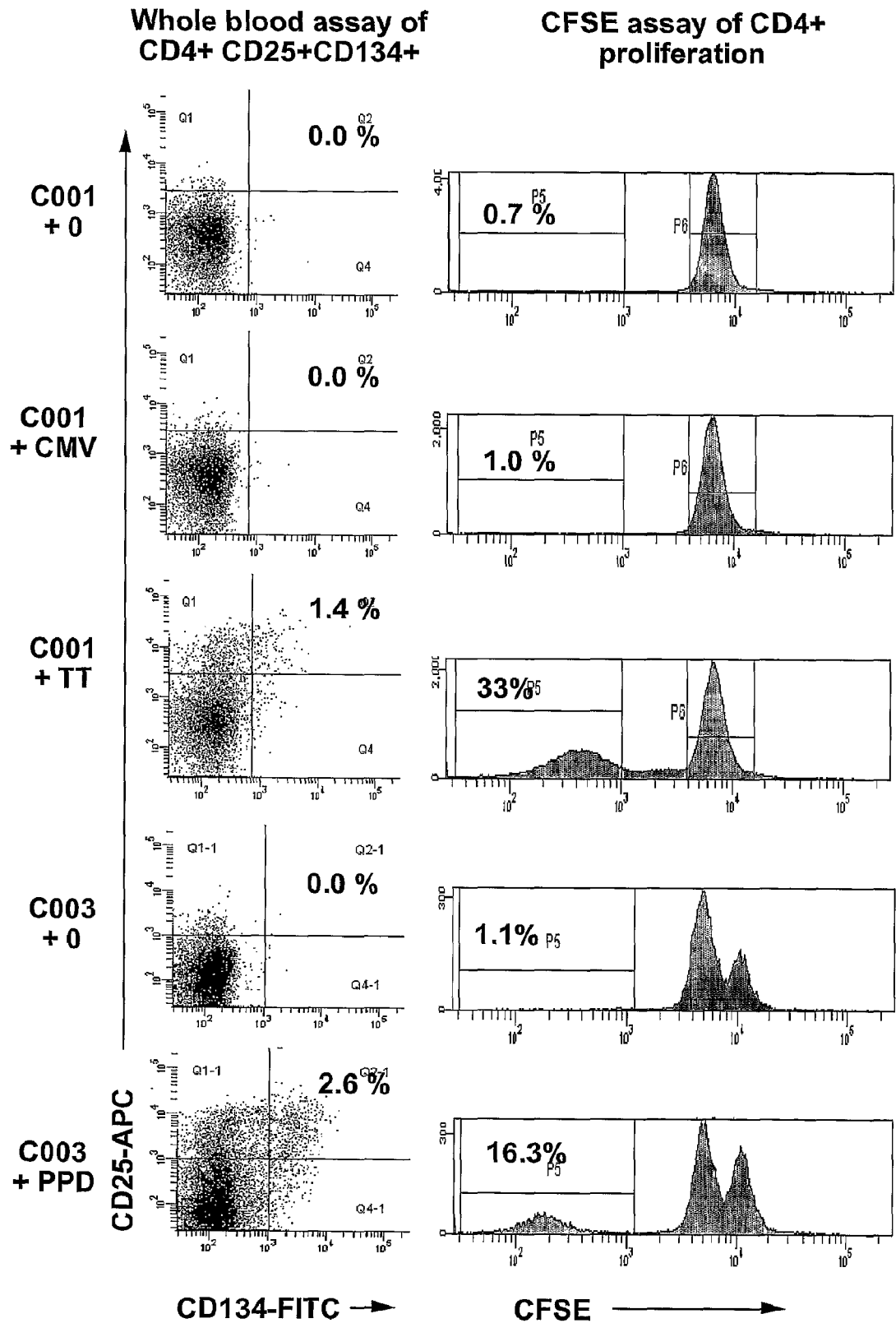
FIG. 3 provides histograms from a healthy adult control subject (C003, from Table 1) showing staining for CD25+ CD134+ CD4+ T cells (after 40 hr of incubation), compared with staining of proliferating CD4+ T cells (defined as having reduced CFSE fluorescence) at day 7, in response to 0, CMV, TT and PPD. The percentage of CD25+CD134+ CD4+ T cells is shown for each histogram (left) and the percentage of CFSE-dim CD4+ T cells is also shown (right).

Comparison of the Whole Blood Assay with the Standard LPA and CFSE Proliferation Assays Four subjects, with differing recall responses to various antigens, including CMV, TT, PPD and HIV p24, were studied comparing this whole blood assay with the two different proliferation assays. Representative flow cytometry histograms are shown in FIG. 3, demonstrating concordance of the whole blood assay with the CFSE assay of CD4+ T cell proliferation. Results for three healthy adult control subjects and for one HIV+ long-term non-progressor (7) are summarised in Table 1. Specificity of the whole blood assay is demonstrated by the observation that two of the three healthy adult control subjects were negative for responses to CMV across all assays, while the third healthy adult control subject was positive across all three assays. In general, the higher the whole blood assay result, the higher the proliferation results, but there did appear to be significant inter-assay variability, even between the two proliferation assays.

Evolution of a Vaccine Response Following Inoculation with Vaccinia

Figure 4A:
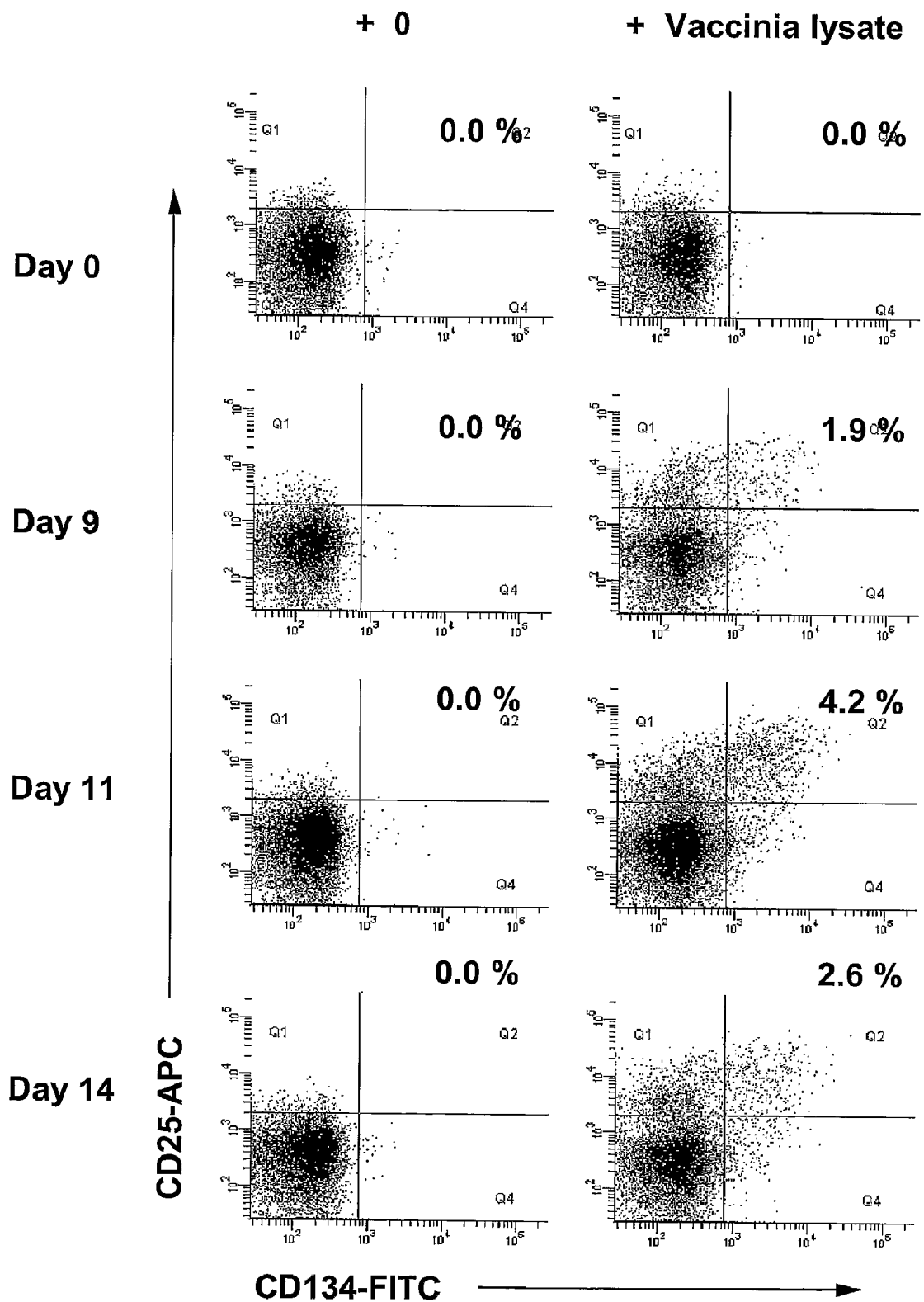
FIG. 4 provides data for the appearance of CD25+CD134+ CD4+ T cells in response to vaccinia inoculation. (A) Representative histograms of staining for CD25+CD134+ CD4+ T cells in whole blood cultures in response to either control (left) or vaccinia lysate (right) at different days following inoculation, for subject VS001. Percentages of CD25+ CD134+ CD4+ T cells are shown for each histogram. (B) Results of staining for CD25+CD134+ CD4+ T cells, in response to vaccinia lysate, for three different subjects following inoculation. (C) Correlation of staining for CD25+ CD134+ CD4+ T cells, compared with intracellular cytokine assay for IFN-γ, in response to vaccinia lysate, for three different subjects following inoculation.
Figure 4B:
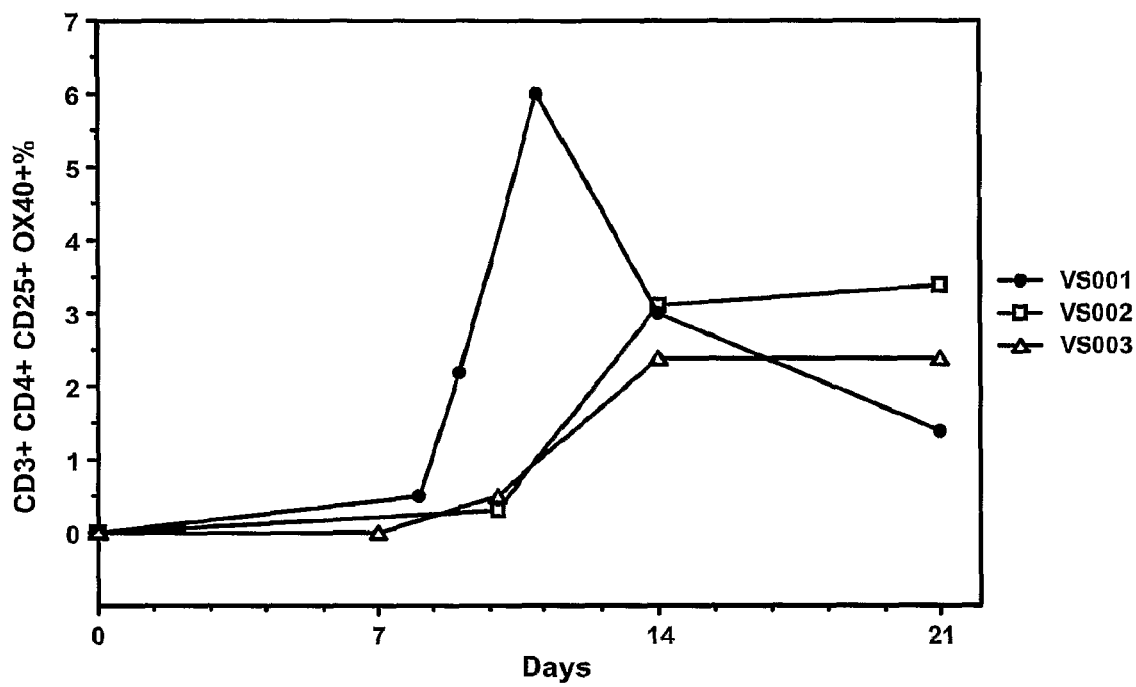
Figure 4C:
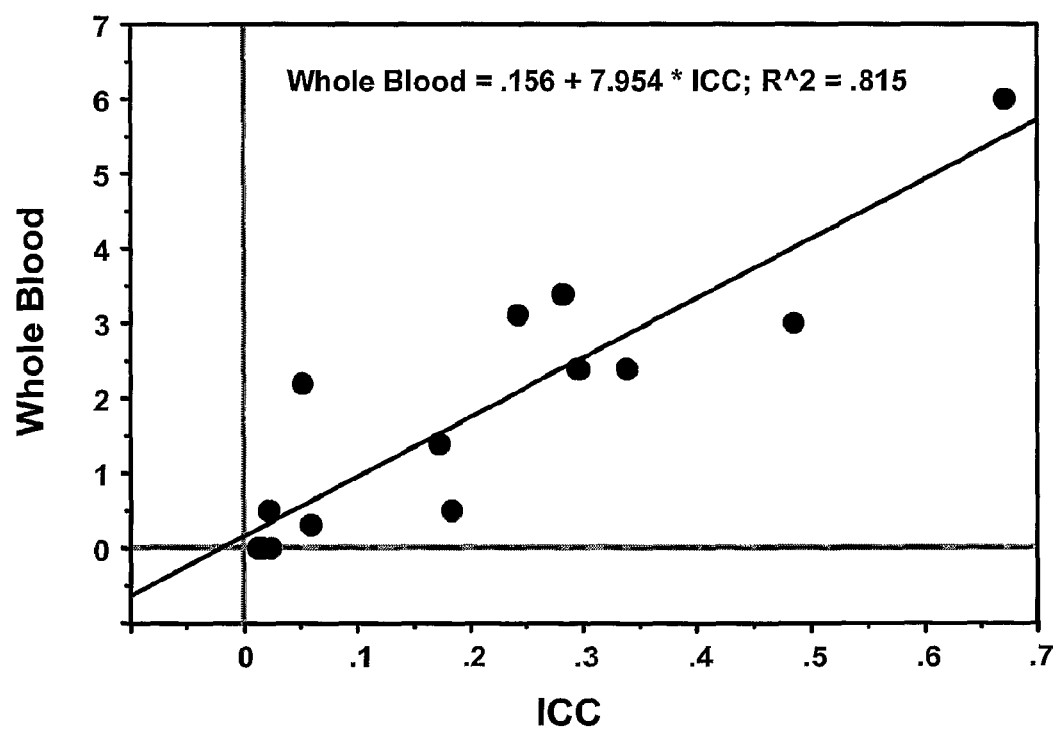

Representative histograms showing the development of a response to vaccinia, following inoculation of a vaccine-naïve subject, detected by the whole blood assay, are shown in FIG. 4A. The longitudinal vaccinia-specific whole blood assay results for 3 different vaccine-naïve subjects are summarised in FIG. 4B, showing a similar pattern of development of responsiveness following inoculation of all vaccinees. FIG. 4C shows the correlation of the vaccinia-specific whole blood assay results versus the ICC assay results (reported in detail elsewhere; 10), across all the longitudinal whole blood samples. There is a very strong correlation between the two assays, with the intercept of the regression line very close to zero. However, the whole blood assay appeared to detect 8-fold more antigen-specific cells. This higher number of antigen-specific CD4+ T cells is much closer to the number of presumptive antigen-specific CD4+ T cells identified by immunophenotyping (10). This is consistent with previous observations that the ICC results during primary HIV-1 and primary CMV infections were approximately 10-fold lower than presumptive antigen-specific CD4+ T cells by immunophenotyping (8).

TABLE 1

Concordance of whole blood CD4+CD25+CD134+ assay, CFSE assay of CD4+ proliferation and lymphoproliferation assay (LPA)

| Subject | Antigen | CD25+CD134+ % of CD4 | CFSE proliferation % of CD4 | LPA Stimulation Index |
|---|---|---|---|---|
| C001 | 0 | 0.0 | 0.7 | 1.0 |
|  | CMV | 0.0 | 1.0 | 0.9 |
|  | TT | 1.4 | 33.4 | 45.4 |
| C002 | 0 | 0.0 | 1.0 | 1.0 |
|  | CMV | 0.1 | 30.6 | 10.3 |
|  | TT | 3.4 | 13.1 | 25.1 |
| C003 | 0 | 0.0 | 2.6 | 1.0 |
|  | CMV | 0.0 | 2.9 | 1.0 |
|  | TT | 2.7 | 51.5 | 139 |
|  | PPD | 2.6 | 16.3 | 42.7 |
| HIV+ LTNP-001 | 0 | 0.0 | 4.0 | 1.0 |
|  | HIV p24 | 5.9 | 50 | 75 |

Discussion

The results demonstrate that the whole blood CD25/CD134 assay of antigen-specific CD4+ T cells has an extremely low background, achieved by the unique simultaneous detection of these two molecules by antibodies to these two cell surface markers. It is well known that a significant proportion of circulating CD4+ T cells express a comparatively low level of CD25, and there is often a small number of cells expressing a very low level of CD134 (data not shown). However, virtually no CD4+ T cells express both antigens ex vivo. Thus it is possible, against this very low background, to detect rare antigen-specific CD4+ T cells.

The results show that CD25+CD134+ CD4+ T cells can be readily detected in such cultures at 24 to 40 hr. The exemplified assay has a number of the advantages of the previous whole blood CD69 assay, namely: (i) simple addition of antigen or mitogen to a small aliquot of sodium heparin anticoagulated whole blood is all that is required for set up; (ii) cells are incubated in autologous plasma, rather than in the artificial situation of pooled human serum; (iii) cell surface staining only is required, rather than needing fixation and permeabilisation; (iv) sample preparation time and complexity of flow cytometric analysis are minimal. However, the CD25+CD134+ assay has additional advantages: (v) by simultaneous detecting CD25 and CD134 with a combination of antibodies, background staining in control cultures is invariably extremely low; and (vi) by counting only cells simultaneously co-expressing CD25 and CD134 on the cells surface, a very high level of specificity is obtained.

Using the exemplified assay, the present applicant has been able to discriminate between subjects with responses to a diverse range of antigens including viral antigens (i.e. CMV and HIV-1), bacterial antigens (i.e. PPD and TT) and polyclonal mitogens (i.e. PHA and SEB). In all cases, the responses were highly correlated with the current "gold standard" assay, the LPA, using either $^3$H-thymidine or CFSE. In another series of experiments, the whole blood CD25/CD134 assay was also highly correlated with the ICC assay.

Conversely, the whole blood CD25/CD134 assay readily detects the very broad polyclonal response to the mitogens PHA and SEB, making it suitable to use as a simple general assay of T lymphocyte function.

Example 2

Macaque Whole Blood CD25/CD134 Assay

Materials and Methods

Subjects 31 macaques were used in this example. Three different groups were examined, specifically, an unvaccinated control group (11 animals), a group vaccinated with a construct expressing the HIV-1 Gag protein (10 animals), and a group vaccinated with a construct expressing the HIV-1 Gag, Env, and Pol proteins as well as other HIV-1 accessory genes (10 animals).

Constructs

The constructs expressing the HIV-1 Gag protein and HIV-1 Gag, Env, and Pol proteins as well as other HIV-1 accessory genes have been described (12).

Reagents

An overlapping peptide pool of 122 peptides from HIV-1 Gag (8) was used in whole blood cultures at a final concentration of 2 μg of each peptide/1 ml.

The following mouse monoclonal antibodies with specificity for human molecules and which cross-react with monkey molecules were used: anti-CD3 and anti-CD4 (PharMingen, San Diego, Calif., United States of America), anti-CD25 (BD Biosciences, San Jose, Calif., United States of America), and anti-CD134 (BD Biosciences, San Jose, Calif., United States of America).

Intracellular Cytokine (ICC) Assay

A whole blood ICC assay optimised for use in macaques, similar to that described in Example 1 was used to analyse IFN-γ responses in fresh peripheral blood samples obtained from the animals.

Whole Blood CD25/CD134 Assay

The CD25/CD134 assay was performed as described in Example 1 in fresh Na-Heparin anticoagulated peripheral whole blood using a pool of overlapping peptides from HIV-1 Gag as the antigen. The cultured samples were assessed for expression of CD3, CD4, CD25 and CD134 using the monoclonal antibodies mentioned above.

Results and Discussion

Figure 5:
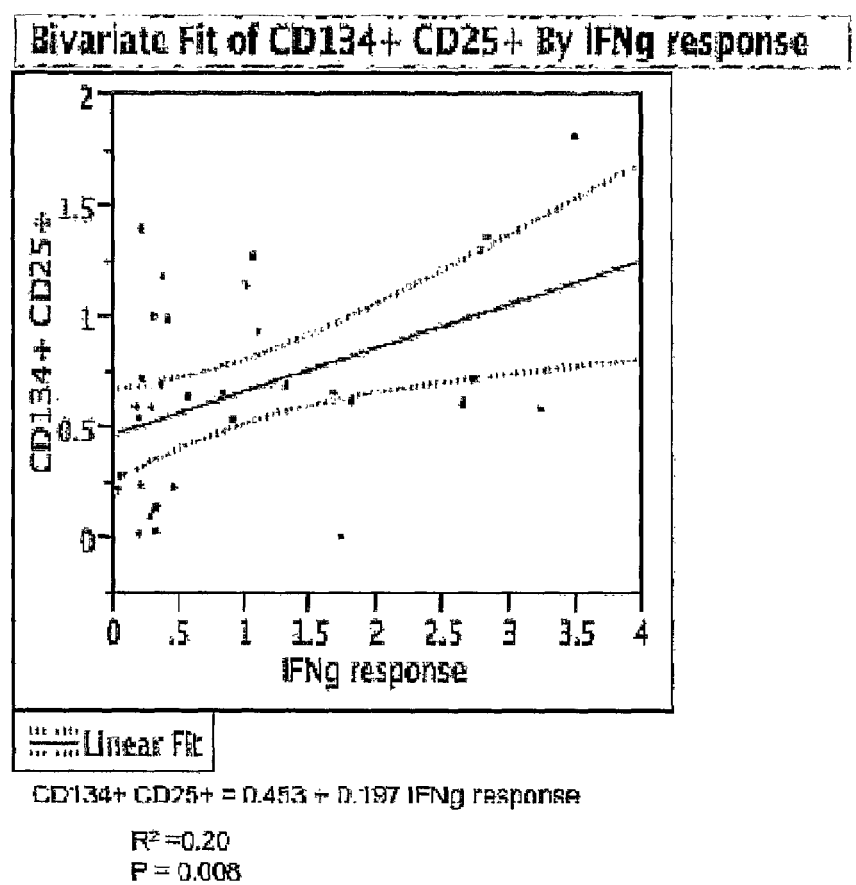
FIG. 5 shows the correlation of staining for CD25+ CD134+ CD4+ T cells, compared with intracellular cytokine assay for IFN-γ, in whole blood from macaques that were either unvaccinated, vaccinated using a construct expressing the HIV-1 group-specific antigen (Gag) protein or vaccinated with a construct expressing the HIV-1 Gag, envelope protein (Env), and Polymerase polyprotein (Pol) proteins and other HIV-1 accessory genes, in response to the HIV-1 Gag antigen peptide pool.

Responses to HIV-1 Gag in CD3+CD4+ T cells from macaque monkeys undergoing vaccination schedules were measured by the whole blood CD25/CD134 assay and compared to IFN-γ responses measured by a standard ICC assay. The comparison of the results, shown in FIG. 5, indicated a clear positive correlation, thereby demonstrating the suitability of the whole blood CD25/CD134 assay for subjects other than humans, particularly non-human primates.

Example 3

Whole Blood CD25/CD137 Assay to Detect Antigen-Specific CD8+ T Cells

Materials and Methods

Subjects

Subjects were recruited as described in Example 1, or may include any subjects whose level of antigen-specific CD8+ T cells or CD8+ T cell-mediated immunocompetence is of interest. For example, subjects that may be of interest include subjects that have been vaccinated against an antigen or exposed to an infectious pathogen, as well as subjects afflicted with a disease or condition, wherein immunity or disease progression is associated with levels of antigen-specific CD8+ T cells (e.g. diseases that require CD8+ cytotoxic T cell (CTL) activity to clear pathogen-infected cells or debris such as infections caused by viruses and other intracellular pathogens, including HIV-1, Hepatitis B and C, Influenza A and B including Avian Influenza, Severe Acute Respiratory Syndrome (SARS) virus, Herpes Simplex Virus (HSV) type I and II, Epstein Barr Virus (EBV), and a range of other viruses, as well as non viral pathogens causing infections such as malaria; hypersensitivity reactions such as that induced by the antiretroviral drug abacavir, in which CD8+ T cells appear to play a significant role in the pathogenesis; and responses to vaccines against viral pathogens especially those induced by DNA vaccines or pox- or adenovirus-based vaccines used either alone or in combination in various prime boost regimes, that are intended to induce a CD8+ T cell response).

Reagents

Antigens and mitogens that may be used are as described in Example 1; however, any number of antigens or mitogens that are well known to persons skilled in the art may be used. For example, antigens or mitogens may include synthesised optimised peptides or overlapping peptide sets, virally infected target cells, such as infected EBV-transformed and immortalised autologous B cell lines, cell lines transfected with MHC-1 molecules of interest, pulsed with peptide sets or infected with viruses, such as vaccinia constructs expressing antigens of interest. The antigens and mitogens used in this experiment were PHA, HIV-1 Gag and a pool of optimised antigenic peptides from CMV, EBV and Influenza virus.

Monoclonal antibodies were used as described in Example 1 and Example 2. However, anti-CD137-PE (BD Biosciences, San Jose, Calif., United States of America) was used in place of the anti-CD134 antibody.

Whole Blood CD25/CD137 Assay

The whole blood CD25/CD137 assay was carried out essentially as described in Example 1. The cultured samples were assessed for expression of CD3, CD8, CD25 and CD137 using monoclonal antibodies and flow cytometry.

Flow Cytometry

Flow cytometry of whole blood cultures was performed on a dual-laser LSR II flow cytometer (Becton-Dickinson) using FACSDiva v4.1 software, as in Example 1. T lymphocytes were first identified using a CD3-PerCP-Cy5.5 vs side scatter gate, followed by gating on CD3+ CD8-APC-Cy7+ T cells. Also, staining with CD4-AlexaFluor700 (Becton Dickinson) was used to exclude CD4+ T cells from the CD8+ T cell gate. CD3+ CD8+CD4− cells were then analysed for binding of CD25-APC and CD137-PE.

Results and Discussion

Responses to PHA, HIV-1 Gag and a pool of optimised antigenic peptides from CMV, EBV and Influenza virus in CD3+CD8+ T cells from either healthy controls or HIV-infected subjects were measured by the whole blood CD25/CD137 assay. In the results shown in FIG. 6, the healthy adult control C002 had a well-defined CD8+ T cell response to CMV, as indicated by tetramer, ICC and Elispot analyses (performed using techniques well-known to persons skilled in the art, data not shown), and yielded a clear positive result in the whole blood CD25/CD137 assay. Conversely, an HIV-infected subject, S009, did not exhibit a CMV response (consistent with his lack of a CD4+ T cell response to CMV; data not shown), but had a clear positive response to HIV Gag peptides, thereby demonstrating the suitability of the whole blood CD25/CD137 assay for study and detection of antigen-specific CD8+ T cells. These results are consistent with the reported involvement of CD137 in memory CD8+ T cell generation and survival in genetic studies in mice (11).

The method of the invention can therefore be used to detect antigen-specific CD8+ T cells by quantitatively or qualitatively measuring the expression of CD25 and CD137 in whole blood samples in response to exposure to an antigen. Accordingly, the method is useful for detecting specific CD8+ T cell responses to antigens of interest, such as those contained in overlapping peptide sets or optimised peptides derived from viral antigens such as CMV, EBV, other herpes viruses, HIV and other retroviruses (Human T-Lymphotrophic Virus (HTLV)-1 and -2, Simian Immunodeficiency Virus (SIV), HIV-SIV recombinant virus (SHIV)), vaccinia viruses either native or recombinant vaccinia or modified vaccinia vectors expressing antigens of interest and other recombinant pox viruses (e.g. fowl pox and avipox viruses), influenza viruses, Hepatitis viruses particularly B and C, parvo viruses, JC viruses, and a range of murine viruses.

Figure 6:
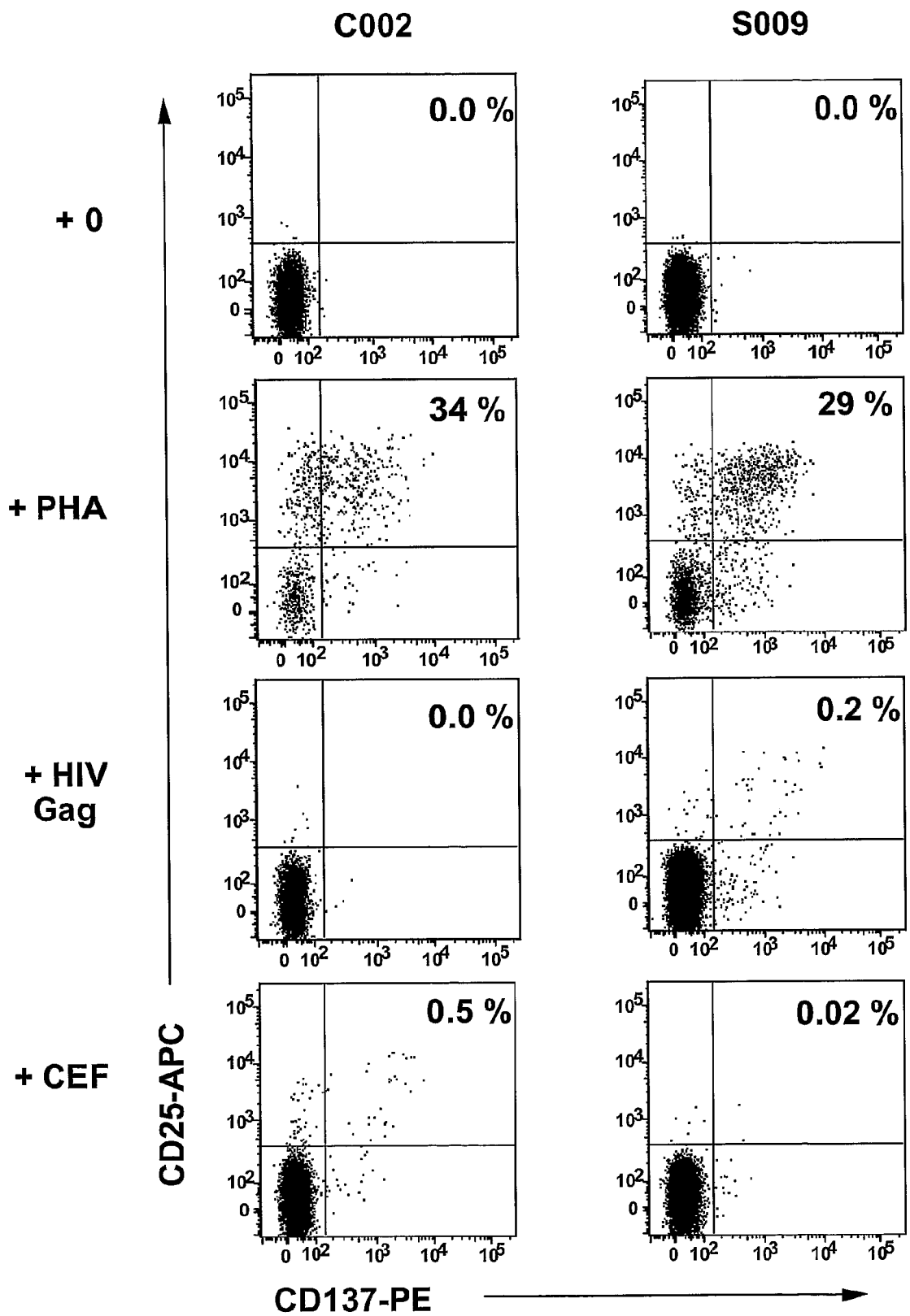
FIG. 6 provides histograms from a representative healthy adult control subject (C002) and a representative HIV+ subject (S009), respectively, showing staining for CD25+ CD137+ CD8+ T cells in the control culture (+0) compared with staining for CD25+CD137+ CD8+ T cells in response to PHA (+PHA); a pool of overlapping peptides from HIV-1 Gag antigen (+HIV Gag); and a pool of optimised antigenic peptides from CMV, EBV and influenza (+CEF), respectively. The percentage of CD25+CD137+ CD8+ T cells is shown for each histogram.

Moreover, the method can also be used in assessing the broader responses to mitogens such as PHA (as shown in FIG. 6), SEB, and anti-CD3 and anti CD28, as a measure of general immunocompetence.

Example 4

Mouse Spleen Cell CD25/CD134 Assay

Materials and Methods

Immunisation of Mice

Four C57BL/6 mice were inoculated subcutaneously with 0.4 mg methyl-Bovine Serum Albumin (mBSA; Sigma, St Louis, Mo., United States of America) emulsified in Complete Freund's Adjuvant (Sigma, St Louis, Mo., United States of America). After 7 days, mice were injected in the right footpad with 200 μg of mBSA, and as control, with PBS in the left footpad. After 24-48 hr, the footpads were examined and maximum swelling measured. Control mice were not inoculated with mBSA. Mice were sacrificed at day 8.

Cell Culture

Spleens from these mice were minced through a sterile 70 μm mesh and single cell suspensions ($1-2\times10^6$ cells/ml) cultured in RPMI 1640 containing 10% fetal calf serum for 44 hours in the presence or absence of 5 μg/ml of methyl-BSA. The mitogen, phytohaemagglutinin (PHA; Sigma, St Louis, Mo., United States of America), was used in additional cultures at a final concentration of 5 μg/ml, as a positive control.

Monoclonal Antibodies and Flow Cytometry

The following monoclonal antibodies with specificity for mouse cell surface antigens were used: anti-CD3-Pacific Blue, anti-CD4 Alexa Fluor 700, anti-CD25-APC and anti-CD134-PE (PharMingen, San Diego, Calif., United States of America).

Cells were stained and analysed on an LSR II flow cytometer as described in Example 1.

Results and Discussion

In immunised mice, footpad swelling 24-48 hr after intradermal challenge with methyl-BSA confirmed the mice had reacted to methyl-BSA in vivo (Jiang et al, unpublished; data not shown). A day later, these mice were sacrificed and the spleens removed.

After 44 hr of spleen cell culture in vitro with PHA, the mean percentage of CD4+ T cells that were CD25+ CD134+ was 66% for all mice. For spleen cells from immunised mice that were cultured with methyl-BSA, the mean percentage of CD4+ T cells that were CD25+ CD134+ was 1.81%. For spleen cells from control, unimmunised mice, the mean percentage of CD4+ T cells that were CD25+CD134+ was 0.04%. These results demonstrate that the CD25/CD134 assay can also be used to detect antigen-specific CD4+ T cells in mice.

In summary, the exemplified whole blood CD25/CD134 and CD25/CD137 assays have several advantages over present methods, including ease of culture set up (i.e. no need to prepare PBMC), simplicity of preparation for analysis (cell surface antigens only), simplicity of flow cytometry analysis (four-colour analysis, which can be run on the vast majority of flow cytometers currently in use in clinical laboratories), coverage of a very broad range of responses (from rare antigen-specific cells to polyclonal responses to mitogens) and may make use of small blood volumes which is an advantage especially in paediatric populations. Further, the assays may allow for transport of samples post fixation such that the assays can be set up off-site, but with detection by flow cytometry conducted at a specialist centre.

The CD25/CD134 and CD25/CD137 assays are suitable for a variety of applications including:

1. Determination of general immunodeficiency by measurement of response to a mitogen (e.g. PHA);
2. Monitoring responses to pathogens (e.g. common microbial agents and other environmental microbes), for which appropriate antigen preparations are available, such as: bacteria, fungus, viruses and protozoa;
3. Monitoring loss of responses to infections by such pathogens (e.g. CMV) in subjects with advanced immunodeficiency due to HIV-1 infection;
4. Monitoring vaccine responses (e.g. to Vaccinia, TT, BCG (MTB), HIV-1 and measles, mumps and rubella (MMR));
5. Identification of antigen-specific CD4+ T cells for detailed phenotyping (e.g. differentiation markers such as Th1 vs Th2; trafficking markers such as lymph node homing versus gut- or skin-homing; cytokine receptors; and chemokine receptors);
6. Cell sorting of unfixed antigen-specific CD4+ T cells or CD8+ T cells after 44 hr culture (e.g. allowing quantitative single cell cultures, functional assays on purified populations of antigen-specific cells, assessment of activation requirements and differential effects of various antigen presenting cell populations on cell activation/proliferation, for gene profiling, and T cell receptor analysis). Presently, flow cytometric identification of antigen-specific CD4+ T cells for cell sorting usually involves the ICC assay, in which cells are fixed and permeabilised precluding further growth in vitro. In contrast, cells sorted in accordance with the present invention could be used for in vitro work or, perhaps, even in vivo work such as reinfusion experiments in mice, macaques and, potentially in humans. The cells could also be used for the isolation of RNA species for gene profiling.
7. Simple screening for potential antigens from crude mixtures;
8. Monitoring of responses to well-characterised autoantigens, such as nuclear antigens and allergens (e.g. house dust mite proteins or grass pollen proteins);
9. Paediatrics and other situations where blood volumes are limiting; and
10. Detecting antigen-specific or mitogen-activated CD4+ T cells or CD8+ T cells in an animal of veterinary significance (e.g. livestock animals, race horses, and companion animals) or in a laboratory animal (e.g. a mouse or monkey for use as, for example, a model of human disease or in the development of vaccines, or other forms of immunotherapy, either stimulatory or suppressive, wherein it is of particular interest to analyse various aspects of the immune response).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Lyons, A B, and C R Parish. 1994. Determination of lymphocyte division by flow cytometry. J Immunol Methods 171:131.
2. Nomura, L E, J M Walker, and H T Maecker. 2000. Optimization of whole blood antigen-specific cytokine assays for CD4(+) T cells. Cytometry 40:60.

3. Suni, M A, H S Dunn, P L Orr, R de Laat, E Sinclair, S A Ghanekar, B M Bredt, J F Dunne, V C Maino, and H T Maecker. 2003. Performance of plate-based cytokine flow cytometry with automated data analysis. BMC Immunol 4:9.
4. Buckley, R H 2004. Molecular defects in human severe combined immunodeficiency and approaches to immune reconstitution. Annu Rev Immunol 22:625.
5. Perfetto, S P, T E Hickey, P J Blair, V C Maino, K F Wagner, S Zhou, D L Mayers, D St Louis, C H June, and J N Siegel. 1997. Measurement of CD69 induction in the assessment of immune function in asymptomatic HIV-infected individuals. Cytometry 30:1.
6. Croft, M 2003. Co-stimulatory members of the TNFR family: keys to effective T-cell immunity? Nat Rev Immunol 3:609.
7. Zaunders, J J, W B Dyer, B Wang, M L Munier, M Miranda-Saksena, R Newton, J Moore, C R Mackay, D A Cooper, N K Saksena, and A D Kelleher. 2004. Identification of circulating antigen-specific CD4+ T lymphocytes with a CCR5+, cytotoxic phenotype in an HIV-1 long-term non-progressor and in CMV infection. Blood 103:2238.
8. Zaunders, J J, M L Munier, D E Kaufmann, S Ip, P Grey, D Smith, T Ramacciotti, D Quan, R Finlayson, J Kaldor, E S Rosenberg, B D Walker, D A Cooper, and A D Kelleher. 2005. Early proliferation of CCR5+CD38+++ antigen-specific CD4+ Th1 effector cells during primary HIV-1 infection. Blood 106:1660.
9. Lewis, R S. 2001. Calcium signaling mechanisms in T lymphocytes. Ann Rev Immunol 19:497-521.
10. Zaunders J J, Dyer W B, Munier M L, Ip S, Liu J. Amyes E, Rawlinson W, De Rose R. Kent S J, Sullivan J S, Cooper D A, Kelleher A D. 2006. CD127+CCR5+CD38+++ CD4+ Th1 effector cells are an early component of the primary immune response to vaccinia virus and precede development of interleukin-2+ memory CD4+ T cells. J. Virol. 80(20):10151-61.
11. Whitmire, J K and Ahmed, R. 2000. Costimulation in antiviral immunity: differential requirements for CD4(+) and CD8(+) T cell responses. Current Opinion in Immunology 12(4): 448-55.
12. De Rose R, Batten C J, Smith M Z, Fernandez C S, Peut V, Thomson S, Ramshaw I A, Coupar B E, Boyle D B, Venturi V, Davenport M P, Kent S J. 2007. Comparative efficacy of subtype AE simian-human immunodeficiency virus priming and boosting vaccines in pigtail macaques. J. Virol. 81:292-300.

The invention claimed is:

1. A method for the quantitative or qualitative detection of antigen-specific CD4+ T cells in a subject, said method comprising quantitatively or qualitatively detecting co-expression of cell surface markers CD4, CD25 and CD134 by a cell in a whole blood sample from said subject following in vitro exposure of the whole blood sample to an antigen.

2. The method of claim 1 comprising the following steps:
   (i) culturing the whole blood sample from the subject in the presence of the antigen; and
   (ii) quantitatively or qualitatively detecting co-expression of CD4, CD25 and CD134 by a cell in the cultured whole blood sample.

3. The method of claim 1 wherein the antigen is selected from the group consisting of tuberculin, Hepatitis C Virus (HCV) core antigen, HCV nonstructural protein 3 (NS3), cytomegalovirus (CMV) phosphoprotein 65 (pp65), CMV lysate, Herpes Simplex Virus (HSV)-1 lysate, HSV-2 lysate, vaccinia lysate, tetanus toxoid (TT), purified protein derivative (PPD) from *Mycobacterium tuberculosis, Streptococcus* antigen streptokinase, Human Immunodeficiency virus (HIV)-1 p24, and pools of overlapping peptides from HIV-1 Gag, Env, Pol or other HIV-1 accessory proteins.

4. A method for measuring CD4+ T-cell mediated immunocompetence of a subject, said method comprising quantitatively or qualitatively detecting the co-expression of cell surface markers CD4, CD25 and CD134 by a cell in a whole blood sample from said subject following in vitro exposure of the whole blood sample to an antigen, wherein the detection of cells co-expressing CD4, CD25 and CD134 is indicative of the subject having CD4+ T cell-mediated immunocompetence.

5. The method of claim 4 comprising the following steps:
   (i) culturing the whole blood sample from the subject in the presence of the antigen; and
   (ii) quantitatively or qualitatively detecting co-expression of CD4, CD25 and CD134 by a cell in the cultured whole blood sample.

6. The method of claim 4 wherein said step of culturing consists of culturing the whole blood sample in the presence of the antigen.

7. The method of claim 4 wherein the antigen is selected from the group consisting of tuberculin, Hepatitis C Virus (HCV) core antigen, HCV nonstructural protein 3 (NS3), cytomegalovirus (CMV) lysate, CMV phosphoprotein 65 (pp65), Herpes Simplex Virus (HSV)-1 lysate, HSV-2 lysate, vaccinia lysate, tetanus toxoid (TT), purified protein derivative (PPD) from *Mycobacterium tuberculosis, Streptococcus* antigen streptokinase, Human Immunodeficiency virus (HIV)-1 p24, and pools of overlapping peptides from HIV-1 Gag, Env, Pol or other HIV-1 accessory proteins.

8. The method of claim 1 wherein the detecting step is performed within about 24 to 48 hours of commencement of the culturing step.

9. The method of claim 1 wherein the detecting step is performed within about 40 to 44 hours of commencement of the culturing step.

10. The method of claim 1 wherein the whole blood sample is a heparinised whole blood sample.

11. The method of claim 1 wherein the detecting step comprises the use of at least one monoclonal antibody selected from the group of monoclonal antibodies which specifically bind to one of CD25 and CD134.

12. The method of claim 1 wherein the detecting step comprises the use of flow cytometry.

13. The method of claim 1 wherein the method further comprises a step of isolating cells co-expressing CD4, CD25 and CD134.

14. The method of claim 13 wherein the isolating step comprises the use of at least one monoclonal antibody selected from the group of monoclonal antibodies which specifically bind to one of CD25 and CD134.

15. The method of claim 13 wherein the isolating step comprises the use of flow cytometry.

16. The method of claim 1 wherein the subject is human.

* * * * *